(12) United States Patent
Jain et al.

(10) Patent No.: US 6,638,405 B2
(45) Date of Patent: Oct. 28, 2003

(54) GAS SENSOR AND METHOD OF MANUFACTURING THE SAME

(75) Inventors: Kailash C. Jain, Troy, MI (US); Da Yu Wang, Troy, MI (US); Eric J. Detwiler, Davison, MI (US); Paul Kikuchi, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 85 days.

(21) Appl. No.: 09/949,591

(22) Filed: Sep. 10, 2001

(65) Prior Publication Data

US 2003/0047452 A1 Mar. 13, 2003

(51) Int. Cl.[7] .............................................. G01N 27/407
(52) U.S. Cl. ...................... 204/421; 204/426; 204/429
(58) Field of Search ................................. 204/421–429; 205/783.5–785

(56) References Cited

U.S. PATENT DOCUMENTS

| | | | |
|---|---|---|---|
| 3,556,957 A | * | 1/1971 | Toledo et al. |
| 4,136,000 A | * | 1/1979 | Davis et al. |
| 4,169,777 A | * | 10/1979 | Young et al. |
| 4,426,253 A | * | 1/1984 | Kreuz et al. |
| 4,986,880 A | * | 1/1991 | Dorfman |
| 5,334,284 A | * | 8/1994 | Ngo |
| 5,360,528 A | | 11/1994 | Oh et al. |
| 5,389,225 A | | 2/1995 | Aagard et al. |
| 5,433,830 A | | 7/1995 | Kawai et al. |
| 5,474,665 A | | 12/1995 | Friese et al. |
| 5,733,504 A | | 3/1998 | Paulus et al. |
| 5,787,866 A | | 8/1998 | Sugiyama et al. |
| 5,827,415 A | | 10/1998 | Gur et al. |
| 6,179,989 B1 | * | 1/2001 | Kennard et al. |
| 6,182,498 B1 | | 2/2001 | Mizutani et al. |

* cited by examiner

Primary Examiner—T. Tung
(74) Attorney, Agent, or Firm—Jimmy L. Funke

(57) ABSTRACT

One embodiment of a method for producing a gas sensor, comprises: disposing said gas sensor in a basic agent solution comprising a basic agent comprises a hydroxide of a metal selected from the group consisting of Group IA of the Periodic Table of Elements; Group IIA of the Periodic Table of Elements, and combinations comprising at least one of the foregoing basic agents, wherein said gas sensor comprises an electrolyte disposed between and in ionic communication with a first electrode and a second electrode; and disposing said gas sensor in an acidic agent solution.

20 Claims, 10 Drawing Sheets

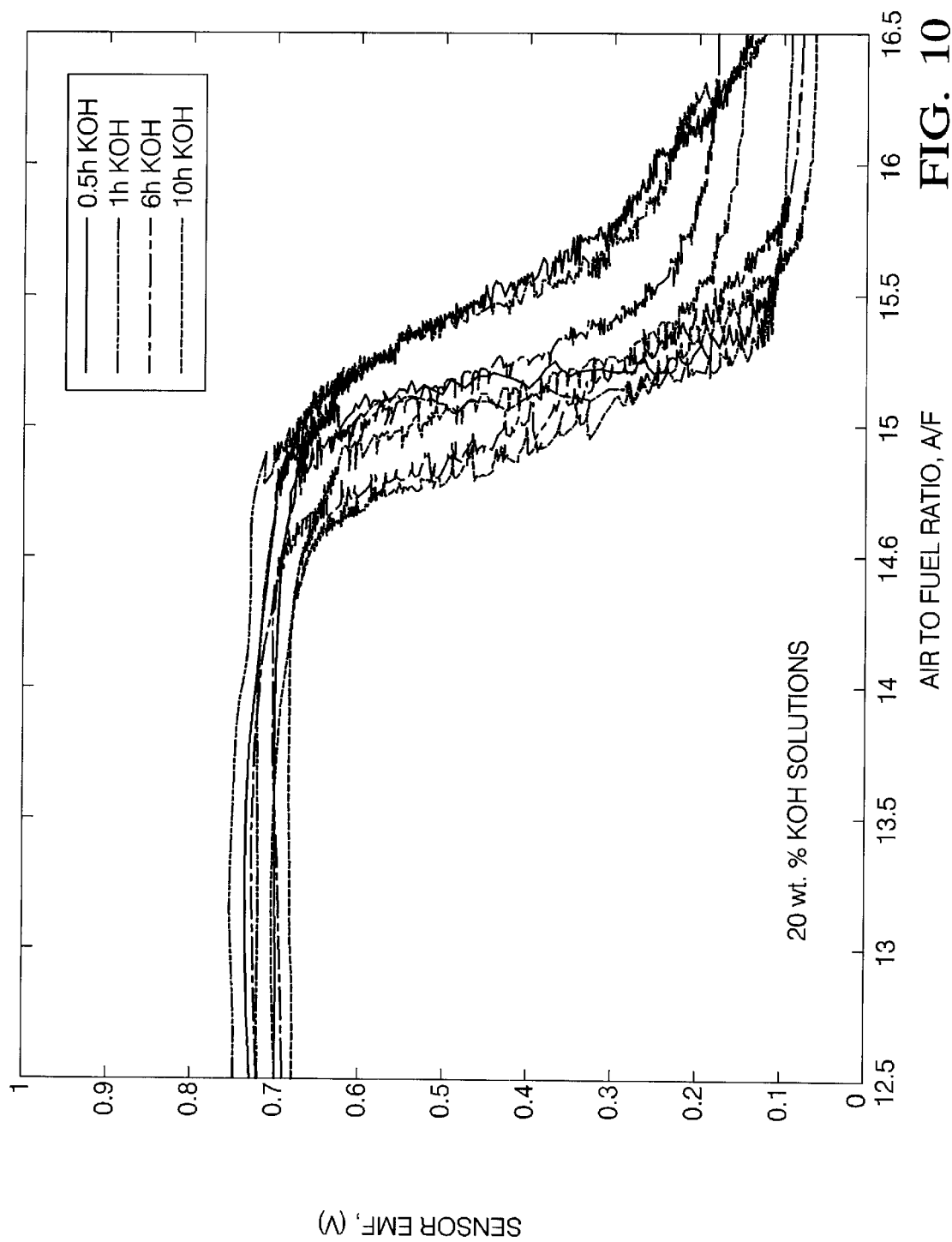

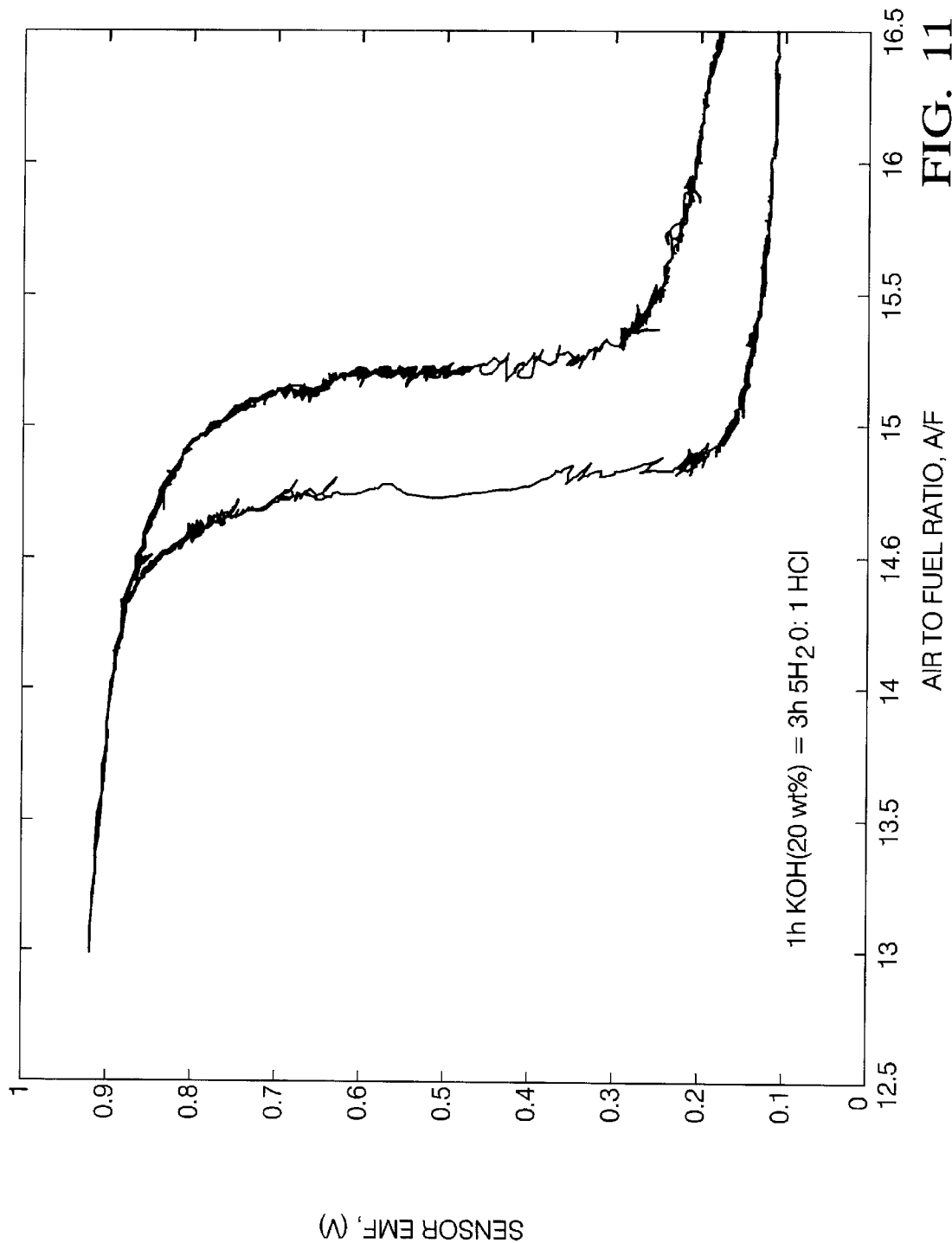

GAS SENSOR AND METHOD OF MANUFACTURING THE SAME

BACKGROUND

Automotive vehicles with an internal combustion engine have an exhaust system including a pathway for exhaust gas to move away from the engine. Depending on the desired operating state, internal combustion engines can be operated with fuel/air ratios in which (1) the fuel constituent is present in a stoichiometric surplus (rich range), (2) the oxygen of the air constituent is stoichiometrically predominant (lean range), and (3) the fuel and air constituents satisfy stoichiometric requirements. The composition of the fuel-air mixture determines the composition of the exhaust gas. In the rich range, considerable quantities of nonburned or partially burned fuel are found, while the oxygen has been substantially consumed and has nearly disappeared. In the lean range, the ratios are reversed, and in a stoichiometric composition of the fuel-air mixture, both fuel and oxygen are minimized.

It is well known that the oxygen concentration in the exhaust gas of an engine has a direct relationship to the air-to-fuel ratio of the fuel mixture supplied to the engine. As a result, gas sensors, namely oxygen sensors, are used in automotive internal combustion control systems to provide accurate oxygen concentration measurements of automobile exhaust gases for determination of optimum combustion conditions, maximization of fuel economy, and management of exhaust emissions.

A switch type oxygen sensor, generally, comprises an ionically conductive solid electrolyte material, a sensing electrode which is exposed to the exhaust gas and reference electrode is subjected to a reference gas such as air or oxygen at known partial pressure. It operates in potentiometric mode, where oxygen partial pressure differences between the exhaust gas and reference gas on opposing faces of the electrochemical cell develop an electromotive force, which can be described by the Nernst equation:

$$E = \left(\frac{RT}{4F}\right) \ln\left(\frac{P^{ref}_{O_2}}{P_{O_2}}\right)$$

where:

E=electromotive force
R=universal gas constant
F=Faraday constant
T=absolute temperature of the gas
$P^{ref}_{O_2}$=oxygen partial pressure of the reference gas
$P_{O_2}$=oxygen partial pressure of the exhaust gas The large oxygen partial pressure difference between rich and lean exhaust gas conditions creates a step-like difference in cell output at the stoichiometric point; the switch-like behavior of the sensor enables engine combustion control about stoichiometry. Stoichiometric exhaust gas, which contains unburned hydrocarbons, carbon monoxide, and oxides of nitrogen, can be converted very efficiently to water, carbon dioxide, and nitrogen by automotive three-way catalysts in automotive catalytic converters. In addition to their value for emissions control, the sensors also provide improved fuel economy and drivability.

Further control of engine combustion can be obtained using amperometric mode exhaust sensors, where oxygen is electrochemically pumped through an electrochemical cell using an applied voltage. A gas diffusion-limiting barrier creates a current limited output, the level of which is proportional to the oxygen content of the exhaust gas. These sensors typically consist of two or more electrochemical cells; one of these cells operates in potentiometric mode and serves as a reference cell, while another operates in amperometric mode and serves as an oxygen-pumping cell. This type of sensor, known as a wide range or linear air/fuel ratio sensor provides information beyond whether the exhaust gas is qualitatively rich or lean; it can quantitatively measure the air/fuel ratio of the exhaust gas.

Due to increasing demands for improved fuel utilization and emissions control, more recent emphasis has been on wide range oxygen sensors capable of accurately determining the oxygen partial pressure in exhaust gas for internal combustion engines operating under both fuel-rich and fuel-lean conditions. Such conditions require an oxygen sensor which is capable of rapid response to changes in oxygen partial pressure by several orders of magnitude, while also having sufficient sensitivity to accurately determine the oxygen partial pressure in both the fuel-rich and fuel-lean conditions.

The temperature of the exhaust gases ranges from ambient temperature, when the engine has not been run recently, to higher than 1,000° C. Since air-fuel ratio output signal depends largely on the exhaust gas temperature, temperature compensation is needed. A heater assists an oxygen sensor, in making more precise measurements over a wide range of exhaust gas temperatures, especially when the exhaust gas temperature is low. The addition of the heater also helps to decrease the light-off time of the sensor, that is the time that it takes for the sensor to reach the minimum temperature for proper operation.

Reduction of light-off times has been accomplished through the use of high power heaters. One method for further decreasing light-off times while using only small or modest heating power is to substantially decrease the size of the sensing element, especially the electrolyte. Similarly, during low temperature operation (e.g., about 350° C. or less), the switching time, or time required for the sensor to detect a change from rich to lean or lean to rich exhaust gas compositions, must be as low as possible, preferably below about a half second (500 milliseconds).

The internal resistance of the sensor is further factor that should be controlled. A low internal resistance or impedance will allow the sensor to sink or source more useful current from the monitoring system that is being used for determining the oxygen content of the exhaust gas.

SUMMARY

A gas sensor and a method for producing the same is disclosed herein. One embodiment of the method comprises: disposing said gas sensor in a basic agent comprises a hydroxide of a metal selected from Group IA or Mg, Ca, Sr, Ba, etc., from Group IIA of the Periodic Table of Elements, and combinations comprising at least one of the foregoing metals, wherein said gas sensor comprises an electrolyte disposed between and in ionic communication with a first electrode and a second electrode; and disposing said gas sensor in an acidic agent solution.

These and other features will be apparent from the following brief description of the drawings, detailed description, and attached drawings.

BRIEF DESCRIPTION OF THE DRAWINGS

Referring now to the following Figures, in which:

FIG. 10 comprises graphs switching characteristics of unheated flat-plate oxygen sensors on a 2.4L twin cam (LD1) engine, exhaust gas at 440° C., after 20 wt % aqueous boiling KOH treatment (a) 0.5 hours (h), (b) 1 h, (c) 6 h, and (d) 10 h; and FIG. 11 comprises graphs of Switching characteristics of an unheated flat-plate sensor on a 2.4L twin cam (LD1) engine, exhaust gas at 440° C., after 1h 20 wt % KOH and 3h $5H_2O:1HCl$ treatment.

DETAILED DESCRIPTION

Although described in connection with an oxygen sensor, it is to be understood that the sensor, which can comprise any geometry (e.g., conical, flat plate, and the like) could be a nitrogen oxide sensor, hydrogen sensor, hydrocarbon sensor, or the like. Furthermore, while oxygen is the reference gas used in the description disclosed herein, it should be understood that other gases could be employed as a reference gas. Additionally, as used herein, unless otherwise stated, "chemically treated" or "cleaned" sensor refers to a sensor treated with both a basic agent solution and an acid agent solution; and an "non-treated", "as sintered" or "as produced" sensor refers to a sensor which did not receive electrical aging, acid, and/or basic treatment after the sintering step.

Figure 1:
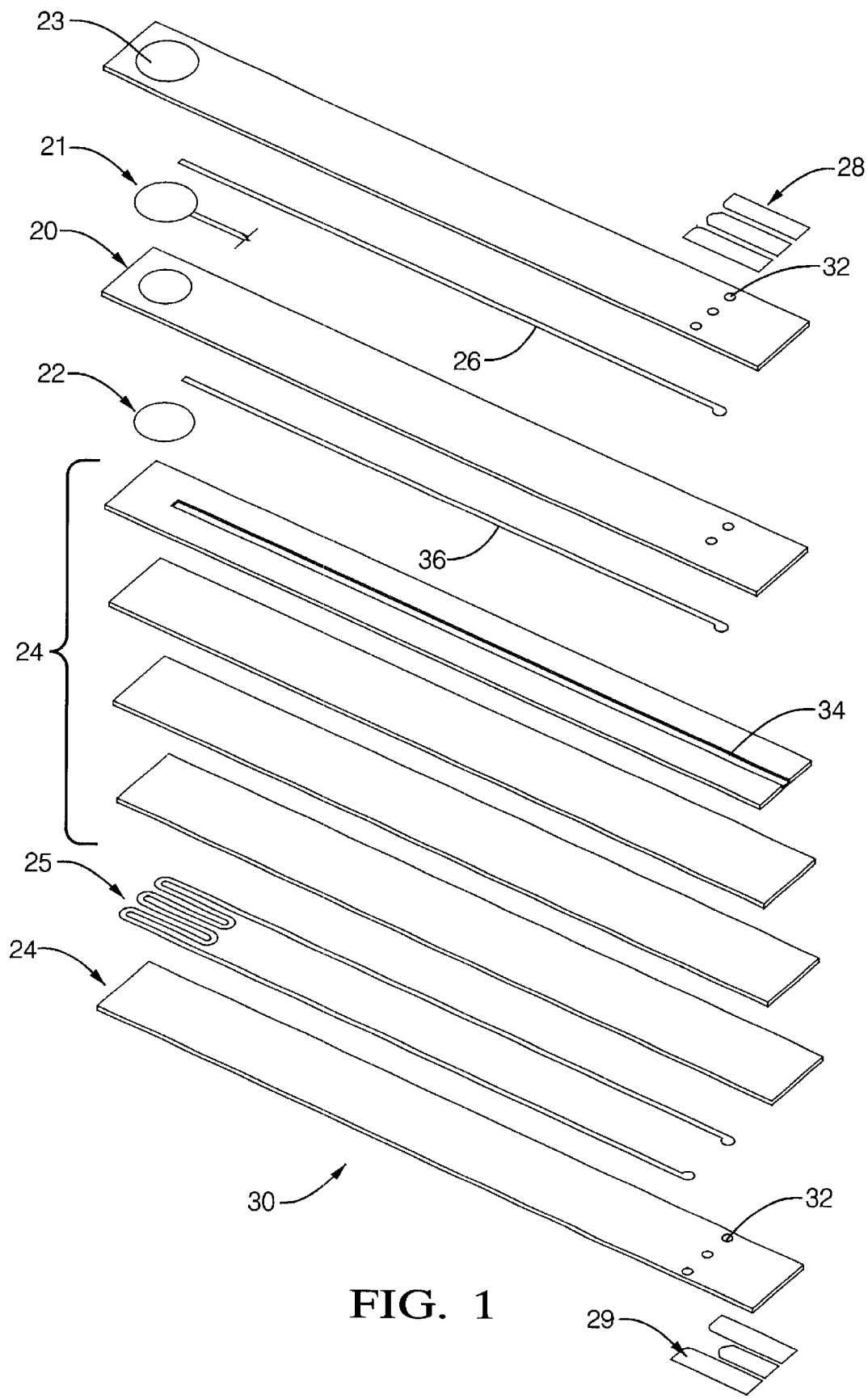
FIG. 1 is an exploded view of a general flat plate type oxygen sensor.

FIG. 1 represents one embodiment of the sensor. FIG. 1 shows a sensor (30) with an ionically conductive solid electrolyte (20), a sensing electrode (21) disposed on one side of the electrolyte (20), between the electrolyte (20) and a porous protective layer (23). On the opposite side of the electrolyte (20) is a reference electrode (22). This side of the electrolyte (20) has an insulator (24), typically alumina, containing a reference gas (e.g., air or the like) channel 34, adjacent to the electrolyte (20) such that reference air contacts electrode (22). Meanwhile, disposed across the electrolyte (20), in electrical communication with the sensing electrode (21) and the reference electrode (22), respectively, are electrical leads (26, 36). On the second side of the reference electrode (22) are support layers (24), and a heater (25). Finally, the outer sides of the sensor (30), at the end opposite the electrodes (21, 22) and electrolyte (20), are contacts (28, 29) which electrically connect to the leads (26, 36) and heater (25) through vias (32). A protective layer (not shown) may also be formed on the second side of the reference electrode (22). Additionally, other sensor components may be employed such as a pumping cell, reference chamber, lead gettering layer, ground plane, porous electrolyte, and the like, as is conventionally known in the art.

The support layers (24), heater (25), contacts (28, 29) and leads (26, 36), can be composed of materials conventionally used in exhaust sensors. For example, the support layers (24) can comprise a dielectric material such as a metal oxide, e.g., alumina, while the heater (25), contacts (28, 29) and leads (26, 36) can comprise a thermally and electrically conductive metal such as platinum, palladium, ruthenium, and the like, and other metals, metal oxides, and alloys and mixtures comprising at least one of the foregoing metals.

The solid electrolyte (20) can be formed of any material that is capable of permitting the electrochemical transfer of oxygen ions while inhibiting the passage of exhaust gases. Possible solid electrolyte materials include conventionally employed materials such as zirconia, ceria, calcia, yttria, lanthana, magnesia, and the like, as well as combinations comprising at least one of the foregoing electrolyte materials, such as yttria doped zirconia and the like.

Disposed adjacent to the solid electrolyte (20) are electrodes (21, 22). The sensing electrode (21), which is exposed to the exhaust gas during operation, preferably has a porosity sufficient to permit diffusion of oxygen molecules therethrough. Similarly, the reference electrode (22), which is typically exposed to a reference gas such as oxygen, air, or the like, during operation, preferably has a porosity sufficient to permit diffusion to oxygen molecules therethrough. These electrodes can comprise any metal capable of ionizing oxygen, including, but not limited to, noble metals such as platinum, palladium, gold, osmium, rhodium, iridium and ruthenium; and metal oxides, such as zirconia, yttria, ceria, calcia, alumina, and the like; as well as combinations comprising at least one of the foregoing metals and metal oxides.

Disposed on the exterior side of the sensing electrode (21) is a protective coating layer (23) which protects the sensing electrode (21) from impurities that cause poisoning of the electrode. The protective coating an comprise a spinel (e.g., magnesium aluminate), alumina, zirconia, and the like, as well as combinations comprising at least one of the foregoing materials.

Essentially, for a planar sensor, the sensor components, e.g., electrodes (21, 22), electrolyte (20), support layers (24), heater (25), leads (26, 36), vias (32), contacts (28, 29), lead gettering layer, ground plane, porous electrolyte, pumping cell, fugitive material (reference chamber), and the like, are formed using techniques such as tape casting methods, sputtering, punching and place, spraying (e.g., electrostatically spraying, slurry spraying, plasma spraying, and the like), dipping, painting, and the like as well as combinations comprising at least one of the foregoing. The components are then laid-up in accordance with the particular type of sensor. The sensor is then heat treated to laminate the layers together. Typically, the sensor is heated to a temperature of about 1475° C. to about 1550° C. for a sufficient period of time to fully fire the layers, with a temperature of about 1490° C. to about 1510° C. preferred, for a period of up to about 3 hours or so, with about 100 minutes to about 140 minutes preferred.

The sintered sensor is subject to chemical treatments using both a basic agent and an acidic agent, preferably in sequence of a basic agent treatment followed by an acidic agent treatment. As the basic agent, an alkali or alkaline earth metal hydroxide can be employed. Possible basic agents include hydroxides of metals in Group IA of the Periodic Table of Elements, Group IIA of the Periodic Table of Elements, and the like, as well as combinations comprising at least on of the foregoing metals. For example, the basic agent comprises sodium hydroxide, lithium hydroxide, magnesium hydroxide, potassium hydroxide, cesium hydroxide, barium hydroxide, strontium hydroxide, calcium hydroxide, and the like, as well as combinations comprising at least one of the foregoing basic agents, with potassium hydroxide and sodium hydroxide preferred. The concentration of basic agent in the basic agent solution, which is preferably an aqueous solution, can be up to the solubility level of the basic agent, with less than or equal to about 45 weight percent (wt %) preferred, less than or equal to about 25 wt % more preferred, and less than or equal to about 20 wt % especially preferred, balance water. It is further preferred to employ a basic agent solution comprising greater than or equal to about 2 wt % basic agent, with greater than or equal to about 3 wt % basic agent more preferred, and greater than or equal to about 5 wt % basic agent especially preferred.

The acidic agent solution can comprise hydrochloric acid (HCl) in a concentration of up to the solubility level of the acidic agent, with less than or equal to about 25 wt % preferred, less than or equal to about 15 wt % more preferred, and less than or equal to about 10 wt % especially preferred, balance water. It is further preferred to employ an acidic agent solution comprising greater than or equal to about 2 wt % acidic agent, with greater than or equal to about 3 wt % acidic agent more preferred, and greater than or equal to about 4 wt % acidic agent especially preferred.

The duration of each treatment, which can be varied between several minutes and several hours, is dependent upon the concentration and temperature of the solution. The temperature of the solutions can individually range from ambient (e.g., about 25° C. or less) to boiling. In order to simplify temperature control of the solutions and process time requirements, the solutions are preferably maintained at boiling. Optionally, between the solution treatments and after the second solution treatment, the sensor can be rinsed with water, preferably deionized water. Finally, the sensor can be dried in a temperature ranging from ambient to a temperature which will not adversely effect the sensor components. To facilitate drying, the sensor is preferably dried at a temperature of about 700° C. to about 900° C., with a temperature of about 750° C. to about 850° C. preferred. It is further preferred to dry the sensor under an inert atmosphere (e.g., nitrogen, argon, helium, and the like, as well as combinations comprising at least one of the foregoing inert atmospheres; e.g., nitrogen with less than or equal to 4 wt % hydrogen.

For example, a sensor can be treated with a 1 hour dip in 20 wt % basic agent (e.g., potassium hydroxide) boiling solution followed by a 3 hour dip in an acidic agent solution (e.g., $5H_2O:1HCl$) boiling solution with appropriate de-ionized water rinses. The sensor can then be dried for 1 hour at 800° C. in a nitrogen atmosphere. The sequential treatment, first with an alkali followed by hydrochloric acid, is designed to optimize the amplitude and rich voltage of the sensor in the exhaust gas.

Figure 2:
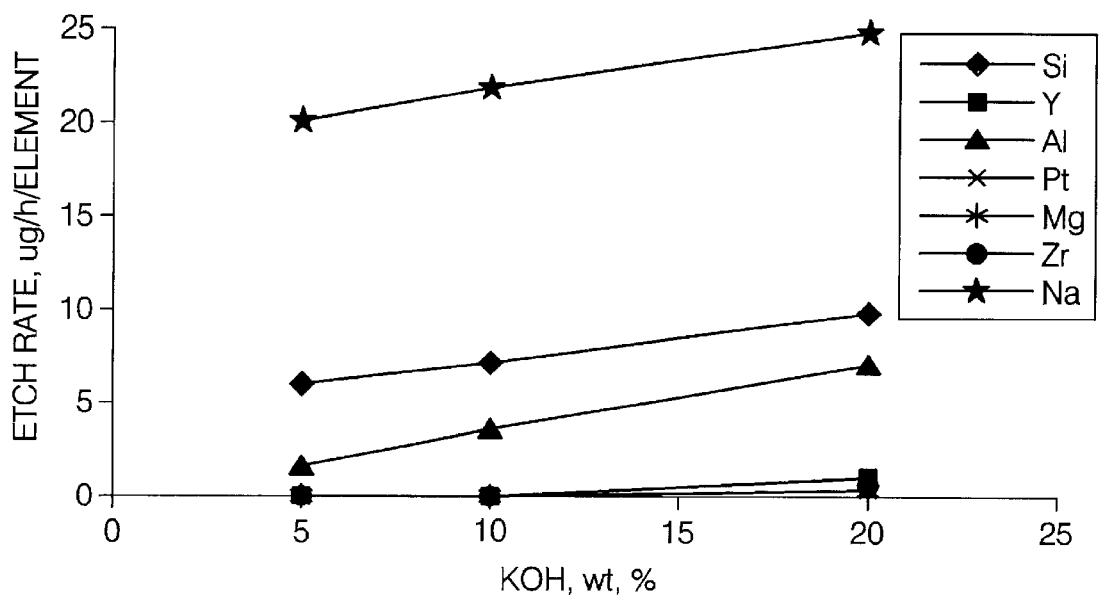
FIG. 2 is a graph illustrating etch or leaching rates of sensor materials and impurities in a potassium hydroxide solutions.
Figure 3:
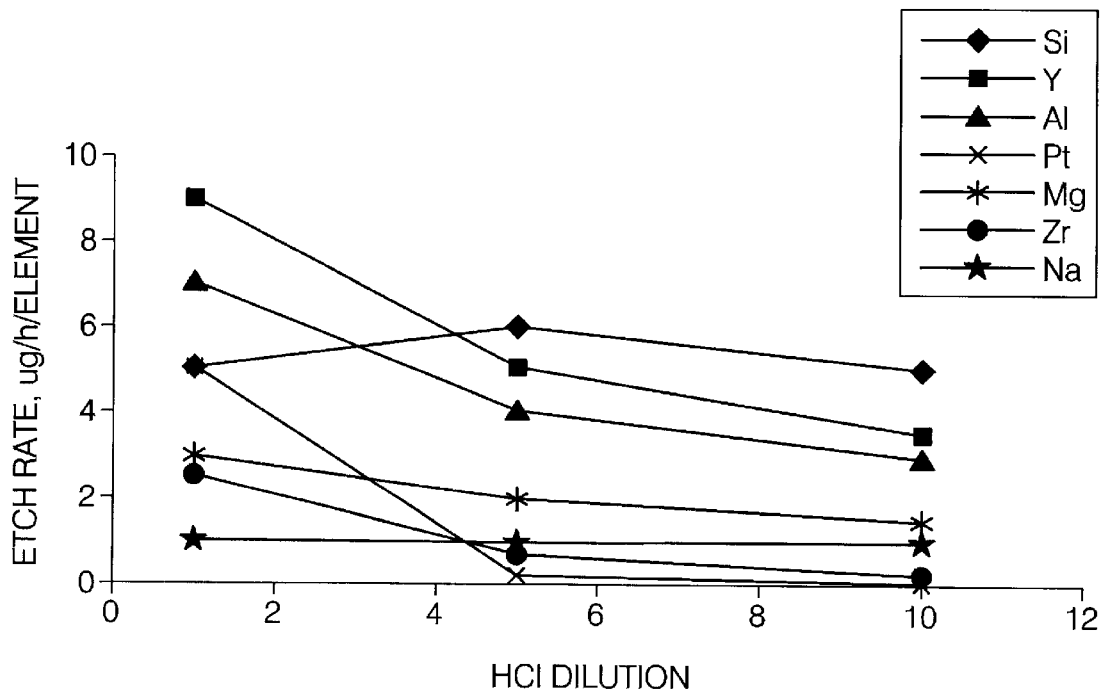
FIG. 3 is a graph illustrating etch or leaching rates of sensor materials and impurities in a hydrochloric acid solutions.

Referring to the figures, FIGS. 2 and 3 graphically illustrate that potassium hydroxide (KOH) solutions are aggressive to materials containing sodium (Na), silicon (Si), and, to a lesser extent, aluminum (Al), but are mild toward zirconium (Zr), yttrium (Y), and platinum (Pt). Similarly, hydrochloric acid solutions containing five parts or more $H_2O$ have higher selectivity for silica than other sensor materials. Therefore, chemical treatments, made using boiling potassium hydroxide and hydrochloric acid solutions, can be employed to selectively remove impurities, while minimally affecting the sensor materials.

Figure 4:
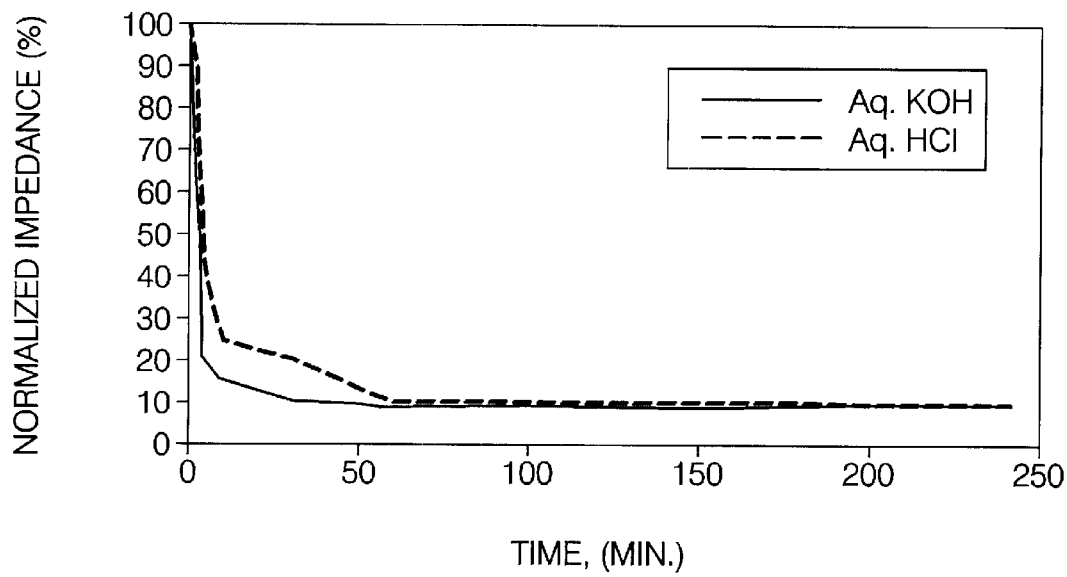
FIG. 4 is a graph illustrating the effect of chemically treating a sensor with potassium hydroxide or hydrochloric acid solution on electrode impedance.
Figure 5:
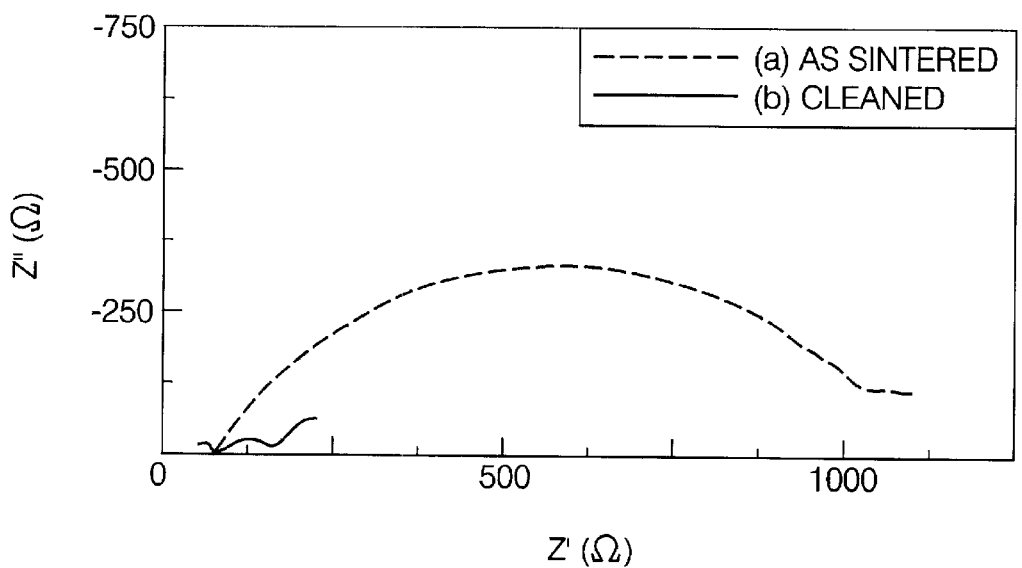
FIG. 5 is an impedance diagram for a chemically treated sensor and a non-treated sensor.

FIGS. 4 and 5 show that the acidic agent and basic agent solutions, individually or in a sequential combination treatment, can reduce the sensor element impedance by over an order of magnitude. In both plots, the sensor heater is maintained at 6.6 W, while, during impedance measurements, a 50 mV ac signal was applied on the electrodes as the frequency was scanned from 2 MHz to 0.1 Hz. FIG. 4 sets forth a graph illustrating normalized impedance of chemically treated electrode. using a 20 wt. % potassium hydroxide solution and 6.3 wt. % hydrochloric acid solution, normalized electrode impedance was measured as a function of time. The graph as shown in FIG. 3 illustrates that chemical treatment greatly reduces impedance, e.g., greater than or equal to about 75% reduction with hydrochloric acid solution, and greater than or equal to about 80% reduction with a potassium hydroxide solution.

In FIG. 5, an impedance diagram for a chemically treated sensor (b) and a non-treated sensor (a) is illustrated. In both tests, the sensor heater was maintained at 6.6 watts (W), while 50 millivolts (mV) alternating current (ac) was applied to the electrodes and the frequency was scanned from 2 megahertz (MHz) to 0.1 hertz (Hz). For the chemical treatment, the sensor was treated with boiling aqueous potassium hydroxide solution (20 wt. %) for 1 hour, then boiling aqueous hydrochloric acid solution (6.3 wt. %) for 3 hours. The chemically treated sensor had a substantially reduced impedance, e.g., less than or equal to about 31 ohms for the chemically treated sensor versus greater than or equal to about 1,100 ohms for the non-treated sensor.

Figure 6:
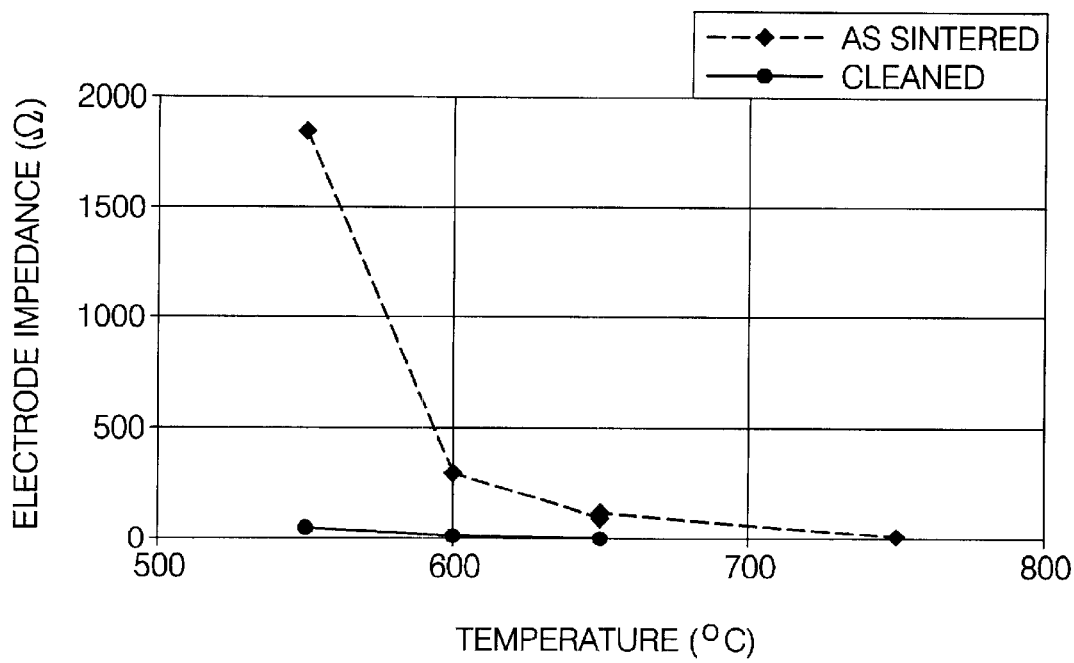
FIG. 6 is a graph of electrode impedance as a function of temperature for an untreated (dashed line) and a chemically treated sensor element (solid line)

FIG. 6 illustrates the temperature sensitivity of the electrode impedance below about 600° C. FIG. 6 is a graph illustrating electrode impedance depending on temperature for a chemically treated sensor and a non-treated sensor. Below about 600° C., electrode impedance is rapidly increased in non-treated sensor, i.e., from about 300 ohms at 600° C. to greater than about 1,750 ohms at 550° C. In contrast, the chemically treated sensor maintained an electrode impedance less than or equal to about 100 ohms at 550° C., with an electrode impedance less than or equal to about 50 ohms at 550° C. preferred. An electrode impedance less than or equal to about 500 ohms at temperatures down to about 260° C. is preferred, with an electrode impedance less than or equal to about 200 ohms at temperatures down to about 260° C. more preferred, and an electrode impedance less than or equal to about 100 ohms at temperatures down to about 260° C. especially preferred. The condition of the chemical treatment was maintained the same as that applied to the sensor in FIG. 5.

Figure 7:
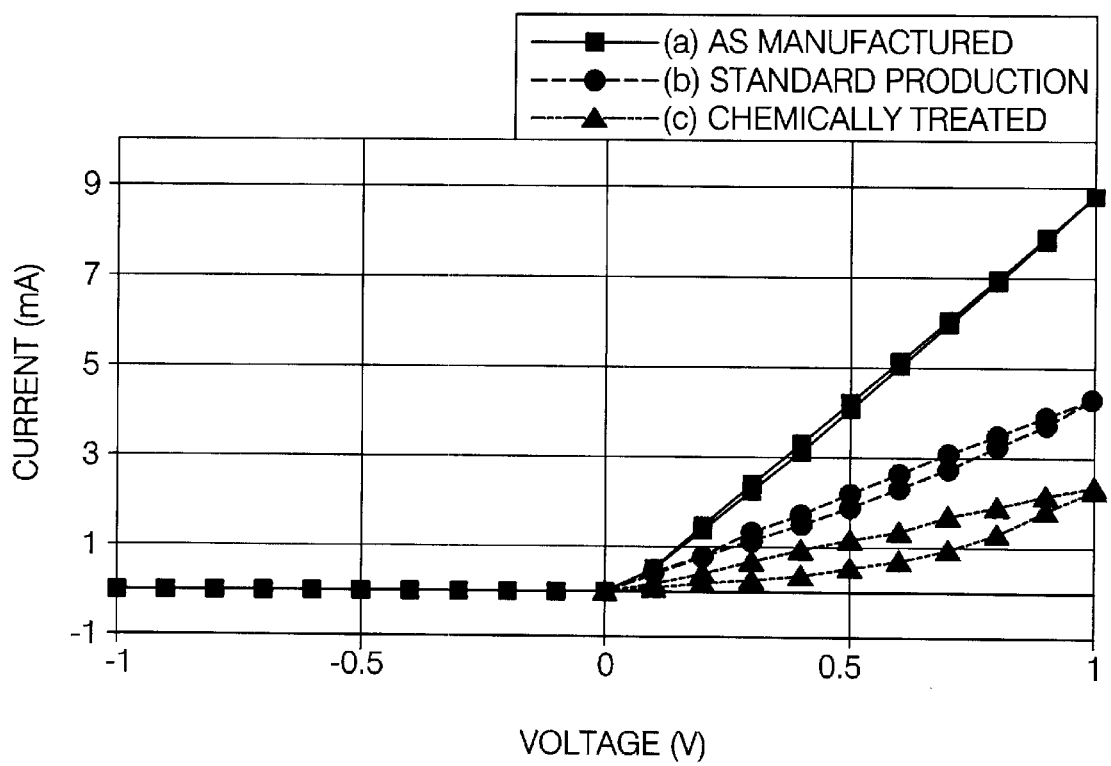
FIG. 7 is a voltage-current plot of sensors for a chemically treated sensor, a non-treated sensor, and electrically aged-hydrofluoric acid treated sensors.

FIG. 7 is a voltage-current plot of sensors for a chemically treated sensor (c), a non-treated sensors (a), and electrical aging-aged and hydrofluoric acid treated sensors (b) when 0 to ±1V were applied to the electrodes to pump oxygen. As can be seen in this figure, at a voltage of 0.5, the chemically treated sensor has a current greater than or equal to about 4 milliamperes (mA), while the non-treated sensor has an average current of less than about 1 mA and the electrical aging-hydrofluoric acid treated sensor has a current to less than or equal to about 2 mA. Similarly, at a voltage of 1, the chemically treated sensor has a current greater than or equal to about 8.5 mA, while the non-treated sensor has an average current of less than about 2.5 mA and the electrical aged and hydrofluoric acid treated sensor has a current to less than or equal to about 4. Consequently, the chemically treated sensor has an improved current of about 200% of the electrical aging-hydrofluoric acid treated sensor current and of about 300% of the non-treated sensor current. The condition of the chemical treatment was maintained the same as that applied to the sensor in FIG. 5. For electrical aging/hydrofluoric acid treatment, after electrical aging, the sensor was dipped for 30 seconds in a 2 wt % hydrofluoric acid solution. Note: for electrical treatment a ±1.5 V square wave pulse 10 second in duration is applied for 5 minutes while the sensor is maintained above 700° C. using an onboard heater powered at 13.5V or higher.

Chemically treated sensors provide higher pump currents than non-treated sensors. For example, chemically treated sensors, employing at heater at 6.6 watts, have a pump current of greater than or equal to about 3 mA at 0.5 volts, with a pump current of greater than or equal to about 3.5 mA at 0.5 volts preferred. Similarly, at 1 volt, with a heater at 6.6 watts, the chemically treated sensor has a pump current of greater than or equal to about 5 mA, with a pump current of greater than or equal to about 7 mA preferred, and a pump current of greater than or equal to about 8.5 mA especially preferred. In contrast, a non-treated sensor, at 1 volt, with a heater at 6.6 watts, has a pump current of less than or equal to about 1 mA.

Figure 8:
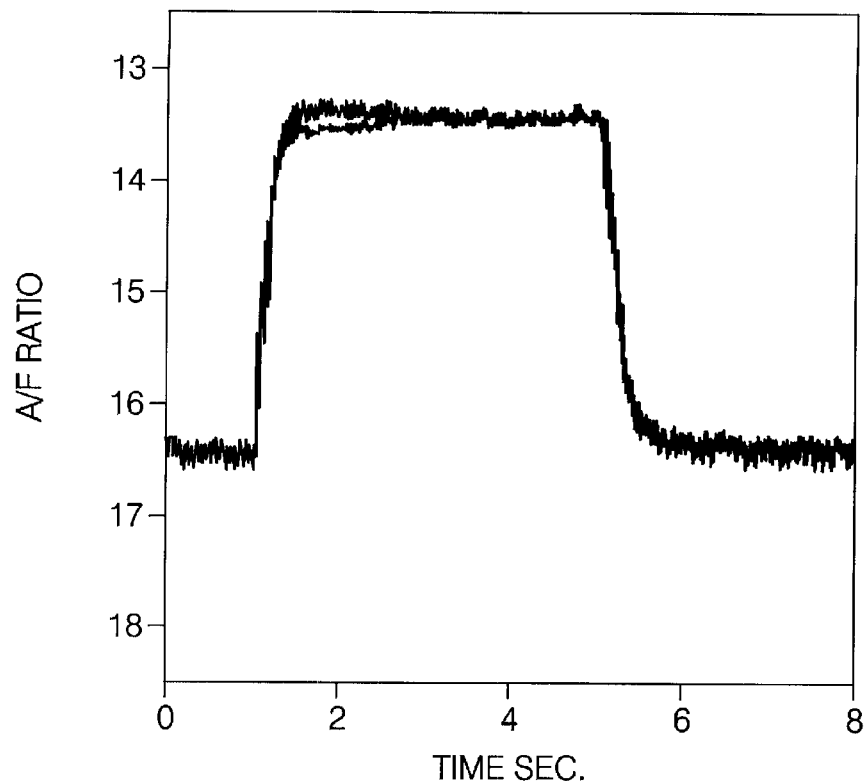
FIG. 8 comprises graphs of an engine performance test (2.4L twin cam LD1) for an electrically aged and HF treated sensor, with the heater maintained at 13.5V, and exhaust gas temperature of 440° C.: (a) air/fuel ratio vs. time variation of exhaust gas as measured by a wide range sensor, superimposed is the response of an electrically aged and HF treated sensor using data from graph (c); (b) static EMF vs. air/fuel for the electrically aged and HF treated sensor showing both rich to lean and lean to rich transitions; (c) sensor voltage vs. time developed by the electrically aged and HF treated sensor upon exposure of a fuel pulse; and (d) dynamic response of this sensor calculated from data of graph (a) superimposed over static response shown in graph (b).
Figure 8:
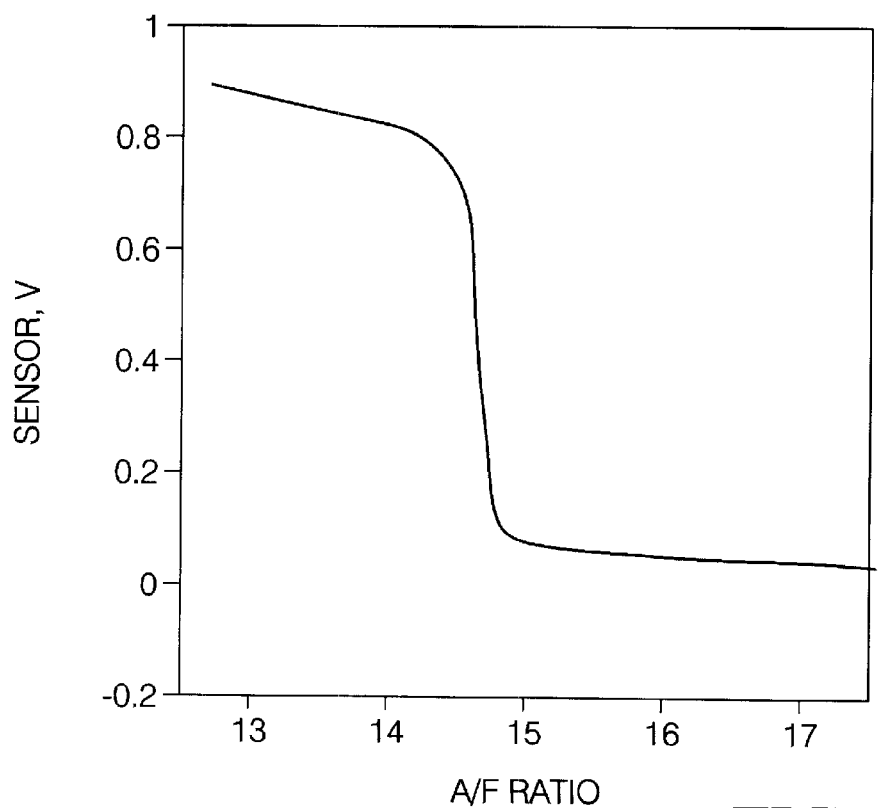
Figure 8:
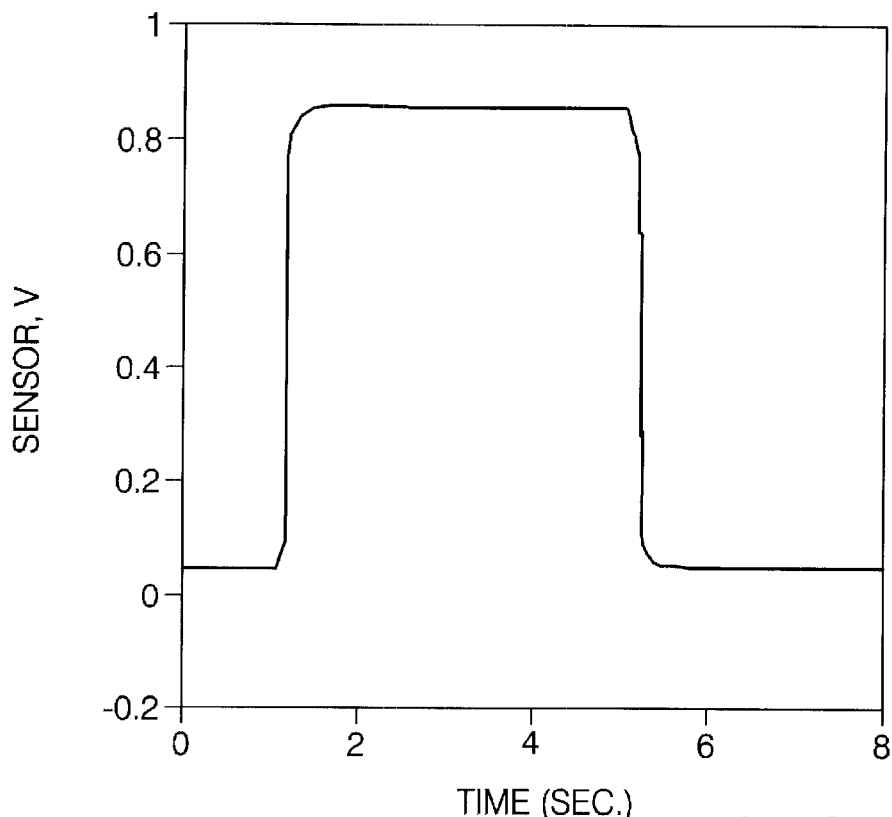
Figure 8:
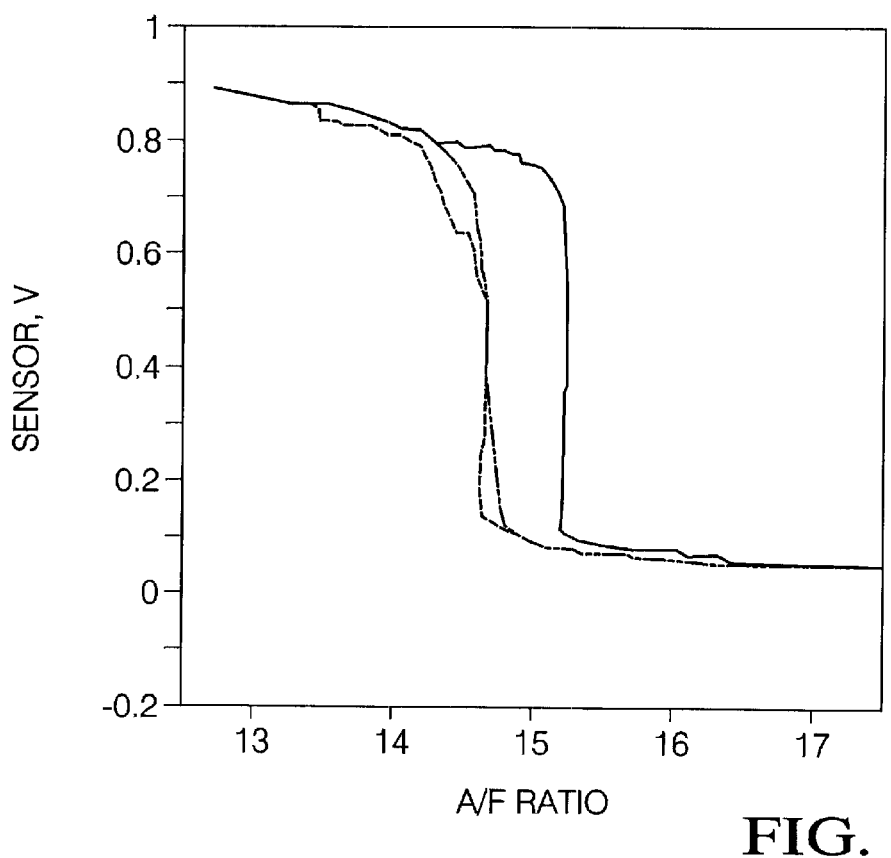
Figure 9:
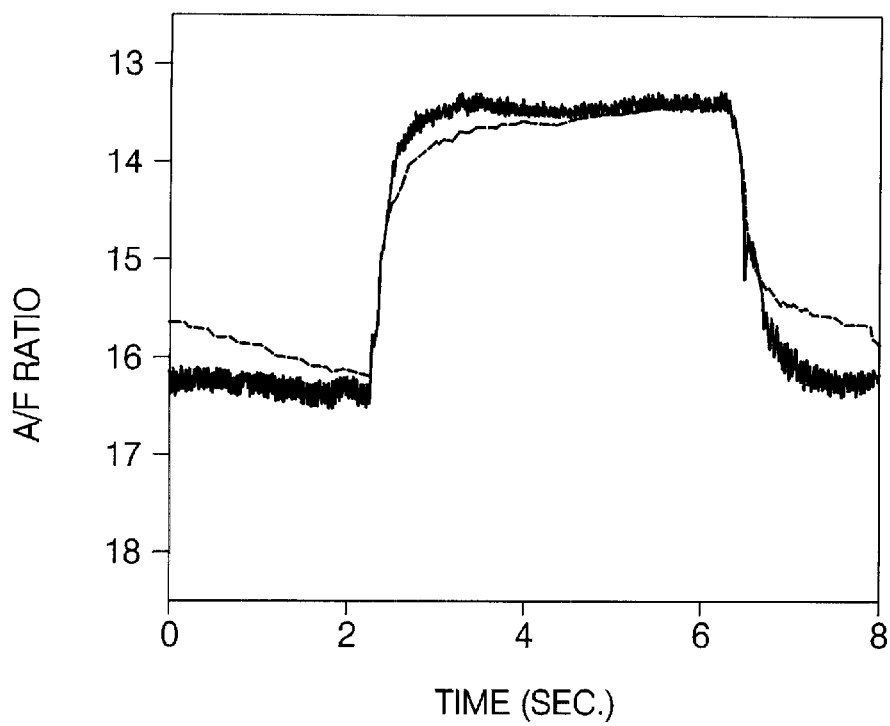
FIG. 9 comprises graphs of an engine performance test (2.4L twin cam -LD1) for a KOH/HCL (or chemically) treated flat-plate sensor, with the heater maintained at 13.5V, and exhaust gas temperature of 440° C.: 9(a) air/fuel ratio vs. time variation of exhaust gas as measured by a wide range sensor, superimposed is the response of the chemically treated sensor using data from graph 9(c); 9(b) static EMF vs. air/fuel for the chemically treated sensor showing both rich to lean and lean to rich transitions; 9(c) sensor voltage vs. time developed by the chemically treated sensor upon exposure of fuel pulse; and 9(d) dynamic response of the chemically treated sensor calculated from data of graph 9(a) superimposed over static response shown in graph 9(b).
Figure 9:
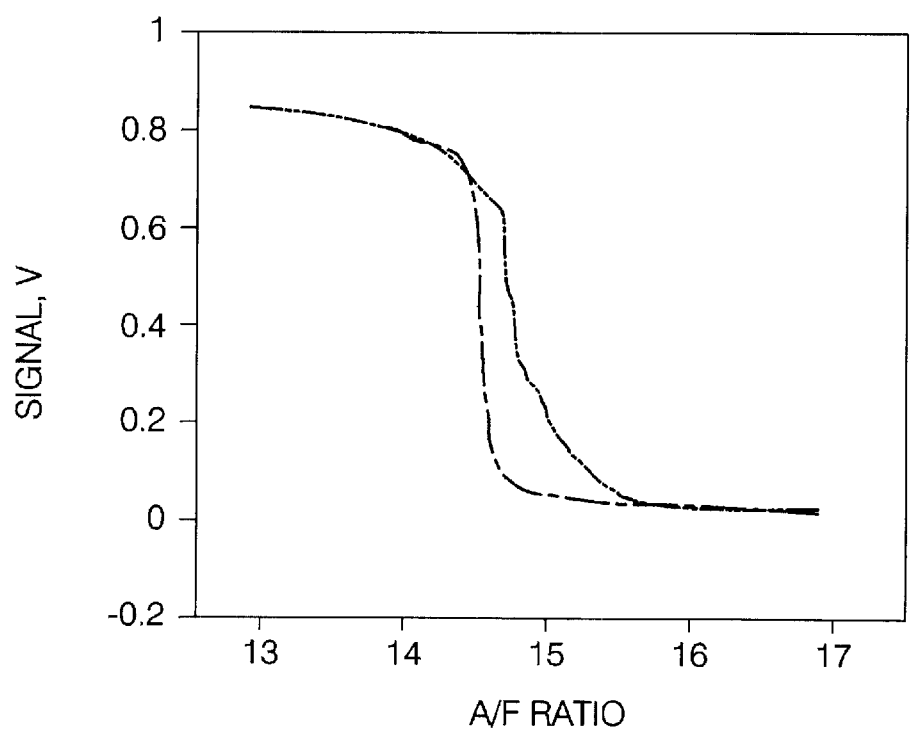
Figure 9:
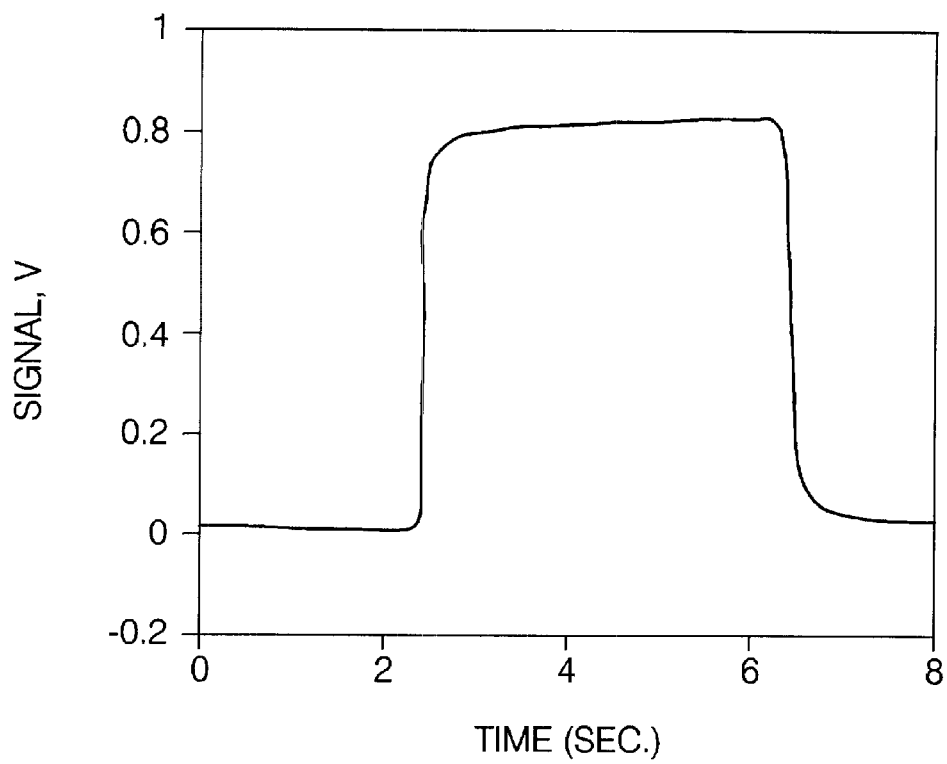
Figure 9:
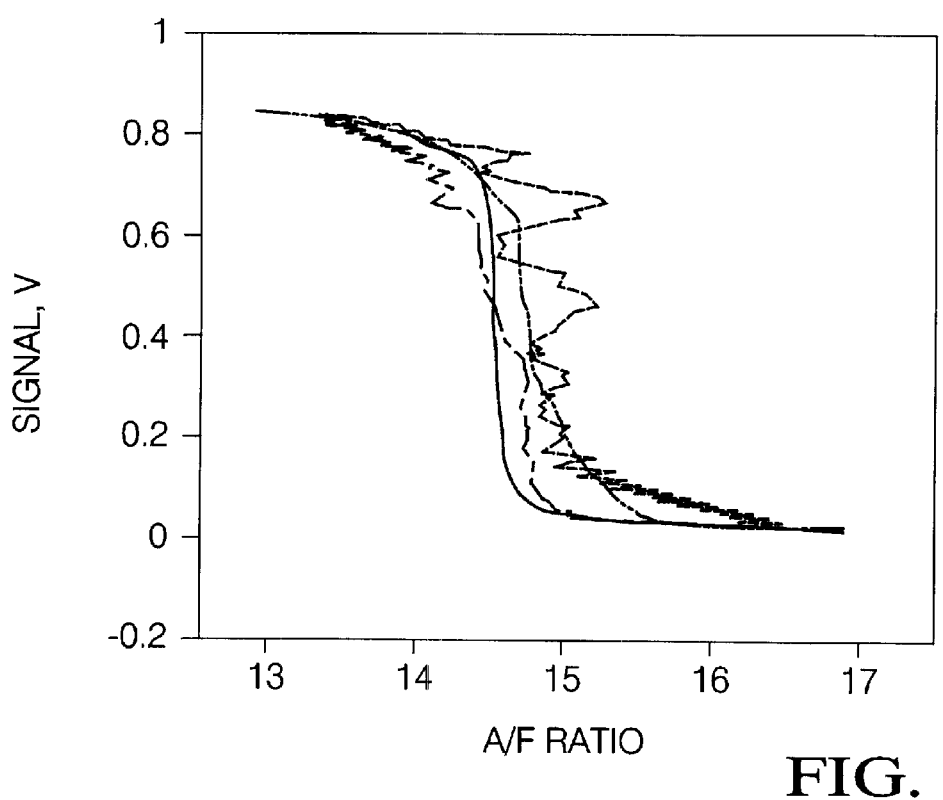

For testing other factors such as switching time, static and dynamic response, and ability of the sensors under test to follow a wide range, chemically treated and electrically aged and hydrofluoric acid treated sensors were packaged for engine tests. FIGS. 8 and 9 illustrate engine performance for standard sensor (electrically aged and hydrofluoric acid treated) and a chemically treated sensor, respectively. For comparison, the same conditions were applied for each test: a 2.4 L twin cam LD1 engine was used, 13.5 V was applied to the heater, and the exhaust temperature was maintained at 440° C. In FIGS. 8(a) and 9(a) air to fuel (A/F) ratio vs. time data was calculated using data from FIGS. 8(c) and 9(c), respectively. Graphs (a) show A/F (Air/Fuel) ratio versus time variation of exhaust gas as measured by a wide-range sensor with that measured by the sensor under test (standard or chemically treated) superimposed thereon; graphs (b) illustrate static EMF (electro-motive force) versus A/F ratio for the test sensor; graphs (c) illustrate time response EMF data on the test (chemically or electrically aged and HF treated) sensor; and graph (d) shows both responses of the test sensors static and dynamic, the later being recalculated from calculated data in graphs (a) for the sensors.

A comparison of FIG. 8 to 9 shows that a chemically treated sensor represented by FIG. 9 follows a wide range sensor more accurately than the sensor represented in FIG. 8, namely an electrically aged and HF treated sensor.

FIG. 10 shows typical results of treating flat-plate sensor elements in boiling aqueous 20 wt % potassium hydroxide (KOH) solution. The solutions were prepared in teflon beakers and stirred during treatment of the sensor elements. Engine tests show that potassium hydroxide has an incubation time, residual effect on transient performance, and not much improvement on rich voltage as compared to a combined potassium hydroxide/hydrochloric acid treatment as shown in FIG. 11.

Sensor structures are often contaminated during manufacturing process due to sintering aids and unintentional impurities in raw materials. By the chemical treatment, especially the sequential basic agent solution followed by acidic agent solution treatment, impurities are removed. The chemical treatment improves the sensor amplitude and eliminates sensor output voltage instabilities, high impedance, and poor switching characteristics by leaching contaminants from sensing electrode, electrolyte, sensing electrode—electrolyte interface, and the reference electrode.

As described above, exhaust sensors provide feed back information that is important for improving the efficiency and performance of a vehicle. The chemically treated exhaust sensor has improved accuracy, reliability, reproducibility and much reduced effect of aging on the engine also known as "green effect".

Chemical cleaning reduces the electrode impedance by a factor of 10 at 550° C. and its sensitivity to temperature and in that respect it is better or at least comparable to electrically aged and hydrofluoric acid treated sensor. Chemical cleaning, however, also improves the electrocatalytic activity of the electrode such that, at 440° C. exhaust gas temperature, the lean to rich response is 3 times and rich to lean time is 2 times improved compared to electrically aged and hydrofluoric acid treated sensors. For a control system to be useful, the sensor should have sufficiently low impedance to shorten the light-off time of the sensor especially at the initial stage of engine operation, (e.g., much less than about 50 kilo-ohms (k$\Omega$) at about 300° C.) when the exhaust gas is still at low temperature. A non-treated sensor has impedance that can exceed about 3 k$\Omega$ below 550° C. and an electrically aged and hydrofluoric acid treated sensor has impedance of about 3 k$\Omega$ at 490° C. In contrast, the chemically treated sensor has an impedance of about 3 k$\Omega$ about 400° C. because of reduced sensitivity of electrode impedance to temperature. While preferred embodiments have been shown and described, various modifications and substitutions may be made thereto without departing from the spirit and scope of the invention. Accordingly it is to be understood that the apparatus and methods have been described by way of illustration only, and such illustrations and embodiments as have been disclosed herein are not to be construed as limiting to the claims.

What is claimed is:

1. A method for producing a gas sensor, comprising:
    disposing said gas sensor in a basic agent solution, wherein the basic agent comprises a hydroxide of a metal selected from the group consisting of Group IA of the Periodic Table of Elements; Group IIA of the Periodic Table of Elements, and combinations comprising at least one of the foregoing metals, wherein said gas sensor comprise; solid electrolyte disposed between and in ionic communication with a first electrode and a second electrode; and disposing said gas sensor in an acidic agent solution: wherein a chemically treated sensor is formed.

2. The method of claim 1, further comprising boiling said basic agent solution and said acidic agent solution.

3. The method of claim 1, wherein said acidic agent solution comprise hydrochloric acid.

4. The method of claim 1, wherein said basic agent solution comprises about 2 wt % to about 45 wt % basic agent, balance water.

5. The method of claim 4, wherein said basic agent solution comprises about 3 wt % to about 25 wt % basic agent.

6. The method of claim 5, wherein said basic agent solution comprises about 4 wt % to about 20 wt % basic agent.

7. The method of claim 1, wherein said acidic agent solution comprises about 2 wt % to about 25 wt % acidic agent, balance water.

8. The method of claim 7, wherein said acidic agent solution comprises about 3 wt % to about 15 wt % acidic agent.

9. The method of claim 8, wherein said acidic agent solution comprises about 4 wt % to about 10 wt % acidic agent.

10. The method of claim 1, further comprising rinsing said gas sensor in water after disposing said gas sensor in said basic solution and before disposing said gas sensor in said acidic solution.

11. The method of claim 1, wherein said chemically treated sensor comprises an electrode impedance of less than or equal to about 100 ohms at 550° C.

12. The method of claim 11, wherein said chemically treated electrode impedance is less than or equal to about 50 ohms at 550° C.

13. The method of claim 1, wherein said chemically treated sensor has a pump current of greater than or equal to about 3 mA at 0.5 volts with a heater at 6.6 watts.

14. The method of claim 13, wherein said chemically treated sensor has a pump current of greater than or equal to about 3.5 mA at 0.5 volts with a heater at 6.6 watts.

15. The method of claim 1, wherein said chemically treated sensor has a pump current of greater than or equal to about 5 mA at 1 volt with a heater at 6.6 watts.

16. The method of claim 15, wherein said chemically treated sensor has a pump current of greater than or equal to about 7 mA at 1 volt with a heater at 6.6 watts.

17. The method of claim 16, wherein said chemically treated sensor has a pump current of greater than or equal to about 8.5 mA at 1 volt with a heater at 6.6 watts after chemical treatment.

18. The method of claim 1, wherein said basic agent is selected from the group consisting of sodium hydroxide, lithium hydroxide, magnesium hydroxide, potassium hydroxide, cesium hydroxide, barium hydroxide, strontium hydroxide, calcium hydroxide, beryllium hydroxide, and combinations comprising at least one of the foregoing basic agents.

19. A gas sensor formed by the method of claim 1.

20. The method of claim 1, wherein said gas sensor is disposed in said basic agent solution prior to being disposed in said acidic agent solution.

* * * * *